United States Patent
Ouwehand et al.

(10) Patent No.: US 8,936,928 B2
(45) Date of Patent: Jan. 20, 2015

(54) PROBIOTICS FOR USE IN REDUCING EOSINOPHILIA AND RESPIRATORY ALLERGIES

(75) Inventors: Arthur Ouwehand, Inga (FI); Nina Rautonen, Espoo (FI); Seppo Jaakko Salminen, Turku (FI); Erika Isolauri, Nurmijarvi (FI)

(73) Assignee: Dupont Nutrition Biosciences APS, Copenhagen (DK)

( * ) Notice: Subject to any disclaimer, the term of this patent is extended or adjusted under 35 U.S.C. 154(b) by 921 days.

(21) Appl. No.: 12/593,279

(22) PCT Filed: Mar. 26, 2008

(86) PCT No.: PCT/IB2008/001503
§ 371 (c)(1),
(2), (4) Date: Apr. 14, 2010

(87) PCT Pub. No.: WO2008/122892
PCT Pub. Date: Oct. 16, 2008

(65) Prior Publication Data
US 2010/0189692 A1 Jul. 29, 2010

Related U.S. Application Data

(60) Provisional application No. 60/920,285, filed on Mar. 26, 2007.

(51) Int. Cl.
*A61K 35/74* (2006.01)
*A23L 1/30* (2006.01)

(52) U.S. Cl.
CPC ............. *A23L 1/3014* (2013.01); *A61K 35/745* (2013.01); *A61K 35/747* (2013.01); *A23V 2002/00* (2013.01); *A23Y 2220/03* (2013.01); *A23Y 2300/49* (2013.01)
USPC ..................................... 435/252.9; 424/93.45

(58) Field of Classification Search
None
See application file for complete search history.

(56) References Cited

U.S. PATENT DOCUMENTS

2010/0166721 A1* 7/2010 Masri .......................... 424/93.44

OTHER PUBLICATIONS

Shamir et al., Journal of the American College of Nutrition, vol. 24, No. 5, pp. 371-375, 2005.*
U.S. Appl. No. 60/804,329.*
Daniel et al., Allergy, 2006, vol. 61, pp. 812-819.*
Flinterman et al., International Archives of Allergy and Immunology, 2007; vol. 143:pp. 237-244, published online Feb. 9, 2007.*
Elfman L. et al., Different profiles in specific IgE to rBet v 1 and rBet v 2 in patients allergic to birch pollen from six countries, Int. Arch. Allergy Immunol., 113:249-511 (1997).
Jarolim E et al., IgE and IgG antibodies of patients with allergy to birch pollen as tools to define the allergen profile of *Betula verrucosa*, Allergy 44:385-395 (1989).
Harmsen HJ et al., Analysis of intestinal flora development in breast-fed and formula-fed infants by using molecular identification and detection method, J. Pediatr. Gastroenterol. Nutr. 30:61-67 (2000).
Gueimonde M. et al., New real-time quantitative PCR procedure for quantification of bifidobacteria in human fecal samples, Appl. Environ. Microbiol., 70:4165-4169 (2004).
Rousseaux C. et al., *Lactobacillus acidophilus* modulates intestinal pain and induces opioid and cannabinoid receptors, Nat. Med., 13:35-37 (2007).
Matsuki T. et al., Development of 16S rRNA-Gene-Targeted Group-Specific Primers for the Detection and Identification of Predominant Bacteria in Human Feces, Applied and Environmental Microbiology, 68:5445-5451 (2002).
Fujiwara et al., "A double-blind trial of *Lactobacillus paracasei* strain KW3110 adminstration for immunomodulation in patients with pollen allergy", Allergology International, 2005, vol. 54, p. 143-148 XP002409882.
Xiao et al., "Effect of probiotic *Bifodobacterium longum* BBS36 in relieving clinical symptons and modulating plasma cytokine levels of Japanese cedar pollinosis during the pollen season. A randomized double-blind, placebo-controlled trial", Journal of Investigational Allergology and Clinical Immunology, 2006, vol. 16, p. 86-93 XP002500162.
Ouwehand, "Antiallergic effects of probiotics", Journal of Nutrition, 2007, vol. 137, p. 794S-797S XP009088742.
Moreira et al., "Allergy in marathon runners and effect of *Lactobacillus* GG supplementation on allergic inflammatory markers", Respiratory Medicine, 2006, vol. 100, p. 1123-1131 XP002500160.
Repa et al., "Mucosal co-application of lactic acid bacteria and allergan induces counter-regulatory immune responses in a murine model of birch pollen allergy", Vaccine, 2003, vol. 22, p. 87-95 XP004471123.
Lee et al., "Anti-inflammatory and anti-allergic effects of kefir in a mouse asthma model", Immunobiology, 2007, vol. 212, p. 647-654 XP002500163.
Harmsen HJ et al., Comparison of viable cell counts and fluroescence in situ hybridization using specific rRna-based probes for the quantification of human fecal bacteria, FEMS Microbiology Letters, 183:125-129 (1999).

* cited by examiner

*Primary Examiner* — Allison Fox
*Assistant Examiner* — Yvonne Pyla
(74) *Attorney, Agent, or Firm* — Steptoe & Johnson LLP

(57) ABSTRACT

The present invention provides probiotic compositions suitable for reducing the incidence and duration of nasal eosinophilia and other parameters associated with birch pollen allergy. In some embodiments, the present invention provides methods and/or compositions suitable for reducing nasal and/or respiratory allergy symptoms. Suitably, such compositions may comprise *L. acidophilus*, *B. lactis* or both.

13 Claims, No Drawings

US 8,936,928 B2

PROBIOTICS FOR USE IN REDUCING EOSINOPHILIA AND RESPIRATORY ALLERGIES

FIELD OF THE INVENTION

The present invention provides probiotic compositions suitable for reducing the incidence and duration of nasal eosinophilia and other parameters associated with birch pollen allergy. In some embodiments, the present invention provides methods and/or compositions suitable for reducing nasal and/or respiratory allergy symptoms.

BACKGROUND OF THE INVENTION

Type 1 allergies have dramatically increased worldwide in recent decades. Indeed, up to 20% of the population of industrialized countries suffers from allergic rhinitis, conjunctivitis and/or bronchial asthma caused by air-borne allergens. Birch pollen is one of the most frequent initiators of tree pollen allergies (See e.g., Jarolin et al., Allergy 44:385-395 [1989]). The major birch pollen allergen is designated as "Bet v 1." More than 90% of sufferers of birch pollen allergies have IgE directed against this allergen (See e.g., Elfman et al., Int. Arch. Allergy Immunol., 113:249-511 [1997]). Despite much research in the treatment and prevention of allergies, there remains a need in the art for easy to administer, effective means of treating and/or preventing nasal and other allergies.

SUMMARY OF THE INVENTION

The present invention provides probiotic compositions suitable for reducing the incidence and duration of nasal eosinophilia and other parameters associated with birch pollen allergy. In some embodiments, the present invention provides methods and/or compositions suitable for reducing nasal and/or respiratory allergy symptoms.

The present invention provides methods for reducing the symptoms of respiratory allergies due to birch pollen exposure. In some preferred embodiments, the present invention provides methods for reducing inflammation and/or eosinophilia associated with exposure to birch pollen comprising administering at least one composition comprising an effective amount of at least one probiotic to an individual under conditions such that said eosinophilia and/or inflammation are reduced upon exposure of said individual to said birch pollen. In some preferred embodiments, the eosinophilia is nasal eosinophilia. In some embodiments, the probiotic comprises a culture of *Lactobacillus*. In some preferred embodiments, the *Lactobacillus* is *Lactobacillus acidophilus*. In some further preferred embodiments, the probiotic further comprises a culture of *Bifidobacterium*. In some additional preferred embodiments, the *Bifidobacterium* is *Bifidobacterium lactis*. In some particularly preferred embodiments, the individual has birch pollen allergy. In some additional embodiments, the individual is pre-disposed to develop birch pollen allergy. In some further embodiments, the individual has not previously exhibited an allergic reaction to birch pollen. In some embodiments, the individual is a child. In some additional embodiments, the administering is nasal or oral.

The present invention also provides methods for reducing birch pollen allergy symptoms comprising administering a composition comprising an effective amount of *Lactobacillus acidophilus* and *Bifidobacterium lactis* to an individual under conditions such that said birch pollen allergy symptoms are reduced, wherein said birch pollen allergy symptoms comprise inflammation and/or eosinophilia. In some embodiments, the eosinophilia is nasal eosinophilia. In some further embodiments, the individual is a child. In some further embodiments, the administering is oral or nasal.

DESCRIPTION OF THE INVENTION

The present invention provides probiotic compositions suitable for reducing the incidence and duration of nasal eosinophilia and other parameters associated with birch pollen allergy. In some embodiments, the present invention provides methods and/or compositions suitable for reducing nasal and/or respiratory allergy symptoms.

In particular, the present invention provides probiotic cultures of *Lactobacillus* and *Bifidobacterium* suitable for use with human subjects. In some particularly preferred embodiments, *L. acidophilus* is provided, while in some alternatively preferred embodiments, *B. lactis* (i.e., *B. animalis* subsp. *lactis*; also referred to as "*B. lactis*" herein) is provided. In still further particularly preferred embodiments, combinations of these organisms are provided.

During the development of the present invention, it was found that significant protective effects in reducing eosinophilia were provided by *L. acidophilus* in combination with *B. lactis*. Furthermore, *B. lactis* was found to have anti-inflammatory effects. In addition to reducing eosinophilia, the administration of these organisms resulted in an increase in Th-1. In some particularly preferred embodiments, a composition comprising relative ratio of *L. acidophilus* (NCFM™ strain) and *B. lactis* (Bl-04 strain) find use in reducing nasal eosinophilia.

During the development of the present invention, the effects associated with the consumption of probiotic products children known to have birch pollen allergy were assessed. These products were administered prior to the onset of pollen season and continued for 4 months. During this double-blind investigation, 48 children (2-10 years) were randomized into two groups. Samples were collected from each child at the beginning of the investigation, at the mid-point, and at the end, in order to assess the degree of nasal eosinophilia present in each individual. In addition, the general health and well-being of each child were assessed. In addition, their cytokine levels (IL-5, IL-10, IL-12, TGF-β(3 and IFN-γ), as well as their IgE levels and CD receptor profiles were analyzed. It is noted that IL-12 and IFN-γ are TH-1 inducing (i.e., pro-inflammatory) cytokines. The allergy symptoms experienced by both groups were recorded and microbiota markers were determined, including the counts of *L. acidophilus* NCFM, *B. lactis* Bl-04, bifidobacteria, lactobacilli, *Bacteroides*, *Eubacterium*, and *Clostridium*, and the levels of faecal organic acids.

Definitions

Unless otherwise indicated, the practice of the present invention involves conventional techniques commonly used in food microbiology, nutritional supplements, pediatric disease, epidemiology, molecular biology, microbiology, protein purification, and industrial enzyme use and development, all of which are within the skill of the art. All patents, patent applications, articles and publications mentioned herein, both supra and infra, are hereby expressly incorporated herein by reference.

Furthermore, the headings provided herein are not limitations of the various aspects or embodiments of the invention, which can be had by reference to the specification as a whole. Accordingly, the terms defined immediately below are more fully defined by reference to the specification as a whole.

Nonetheless, in order to facilitate understanding of the invention, definitions for a number of terms are provided below.

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, preferred methods and materials are described herein. Accordingly, the terms defined immediately below are more fully described by reference to the Specification as a whole. Also, as used herein, the singular terms "a," "an," and "the" include the plural reference unless the context clearly indicates otherwise. It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, the term "food" refers to any nutritional item that provides nourishment to a plant and/or animal. It is not intended that the term be limited to any particular item, as it is used in reference to any substance taken into and assimilated by a plant or animal to keep it alive. It is also not intended that the term be limited to "solid" food, as liquid nourishment is encompassed by the definition. Indeed in some embodiments, liquid nourishment is preferred over solid food items. In some preferred embodiments, the term is specifically used in reference to food for human consumption.

As used herein, the term "feed" refers to any nutritional item that provides nourishment to non-human animals. It is not intended that the term be limited to any particular item, as it is used in reference to any substance taken into and assimilated by a plant or animal to keep it alive. It is also not intended that the term be limited to "solid" food, as liquid nourishment is encompassed by the definition. Indeed in some embodiments, liquid nourishment is preferred over solid food items.

As used herein, the terms "nutritional supplement" and "dietary supplement" refer to any product that is added to the diet. In some particularly preferred embodiments, nutritional supplements are taken by mouth and often contain one or more dietary ingredients, including but not limited to vitamins, minerals, herbs, amino acids, enzymes, and cultures of organisms.

As used herein, the term "neutraceutical" refers to a food/dietary supplement that is believed and/or taken to provide health benefits.

As used herein, the term "probiotic" refers to a live microbial food ingredient that is beneficial to health.

As used herein, the term "prebiotic" refers to a non-digestible food ingredient that beneficially affects a human and/or other animal that ingests the prebiotic. In preferred embodiments, prebiotics selectively stimulate the growth and/or activity of at least one type of bacteria in the intestinal tract, such that the health of the human and/or other animal is improved.

As used herein, the term "synbiotic" refers to a mixture of prebiotics and probiotics.

As used herein, the terms "illness" and "disease" refer to any deviation from or interruption of the normal structure and/or function of any body part, organ, or system that is manifested by a characteristic set of symptoms and signs. The term encompasses conditions with known or unknown etiology and/or pathology.

As used herein, the term "treating" refers to the providing (i.e., "administering") of compositions that result in the improvement, amelioration, and/or remedying of a disease, disorder, or symptom of disease or condition. In some embodiments, the compositions of the present invention are provided to an individual in an effective amount to either reduce the severity of symptoms associated with birch pollen allergy (e.g., eosinophilia and/or inflammation) or prevent the onset of symptoms. In some embodiments, the "reduction" in symptoms is in comparison with the degree of symptoms that occur without administration of the compositions of the present invention, upon exposure of the individual to birch pollen.

As used herein, the terms "oral administration," and "per os" refer to the taking of supplements (and/or supplement-containing foods) by mouth.

As used herein, the terms "nasal administration" refers to the taking of supplements (and/or supplement-containing foods) via the nasal passages. It is intended that the term encompass the administration of nasal drops, sprays, sticks, colloidal suspensions, inhalation compositions, and any other composition suitable for administration via the nasal passages.

As used herein, the terms "prevention of illness" and "prevention of disease" refer to measures taken to avoid the incidence of illness/disease. In some embodiments, "prophylactic" measures are taken in order to avoid disease/illness.

As used herein, the term "symptom of disease" refers to any subjective of disease and/or a patient's condition. It is used in reference to any such evidence as perceived by the patient.

As used herein, the term "sign of disease" refers to an indication of the existence of disease/illness. It is used in reference to any objective evidence of disease that is perceptible to the examining physician and/or other healthcare provider.

As used herein, "effective amount" refers to the quantity of a composition (e.g., probiotic) necessary to achieve the desired effect (e.g., reducing, eliminating and/or prevention allergy-related symptoms including, but not limited to eosinophilia and/or inflammation). Such effective amounts are readily ascertained by one of ordinary skill in the art and are based on many factors, such as the particular probiotic, age of the individual, etc. In some embodiments, the effective amount is that amount of probiotic composition that provides relief from eosinophilia and/or inflammation.

As used herein, the term "morbidity" refers to illness/disease.

As used herein, the term "mortality" refers to death.

As used herein, the term "incidence" refers to the rate at which a certain event occurs, as in the number of new cases of a specific disease that occur during a certain period of time.

As used herein, the term "prevalence" refers to the total number of cases of a specific disease and/or condition in existence in a given population at a certain time.

As used herein, the term "respiratory tract" refers to the system that is involved with breathing. The respiratory tract is often divided into three segments, namely the upper respiratory tract (i.e., nose, nasal passages, paranasal sinuses, throat/ pharynx), the respiratory airways (i.e., larynx, trachea, bronchi, and bronchioles), and the lower respiratory tract (i.e., the lungs, comprised of respiratory bronchioles, alveolar ducts, alveolar sacs, and aleveoli).

As used herein, the term "respiratory disease" refers to any disease of the respiratory tract.

As used herein, the term "eosinophilia" refers to the presence of a greater number of eosinophils than normal. The term is used in reference to nasal eosinophilia, in which there is a greater than normal number of eosinophils in the nasal tissues. The term also encompasses eosinophilia observed in the bloodstream.

As used herein, the term "atopy" refers to the genetic tendency of humans and other animals to develop the classic allergic diseases, including but not limited to atopic dermatitis (e.g., eczema), allergic rhinitis (e.g., "hay fever"), and asthma. Atopy involves the capacity to produce IgE in response to common environmental proteins, including but not limited to house dust mites, grass and tree pollens, non-human animal dander and saliva, and insect venoms, as well as food allergens. Atopy is an allergic hypersensitivity (Type 1 hypersensitivity) reaction with a strong hereditary component.

As used herein, the term "infection" refers to the invasion and multiplication of pathogenic microorganisms in the body.

As used herein, the term "gastrointestinal tract" ("GI") refers to the entire alimentary canal, from the oral cavity to the rectum. The term encompasses the tube that extends from the mouth to the anus, in which the movement of muscles and release of hormones and enzymes digest food. The gastrointestinal tract starts with the mouth and proceeds to the esophagus, stomach, small intestine, large intestine, rectum and, finally, the anus.

As used herein, the term "gastrointestinal flora" refers to the microorganisms that inhabit the gastrointestinal system of humans and other animals. In some particularly preferred embodiments, the term is used in reference to bacterial organisms, but is not intended that the term be so limited.

As used herein, the terms "child" and "children" refers to young human beings under 18 years of age.

As used herein, the term "infant" refers to a child under one year of age. A "neonate" is a recently born infant (i.e., from birth to about four weeks of age).

As used herein, the term "toddlers" refers to children who are learning to walk. Generally, the term is used in reference to young children between one and three years of age.

As used herein, the term "culture" refers to any sample or item that contains one or more microorganisms. "Pure cultures" are cultures in which the organisms present are only of one strain of a particular genus and species. This is in contrast to "mixed cultures," which are cultures in which more than one genus and/or species of microorganism are present. In some embodiments of the present invention, pure cultures find use. For example, in some particularly preferred embodiments, pure cultures of *Lactobacillus* (e.g., *L. acidophilus*) find use. However, in alternative embodiments, mixed cultures find use. For example, in some particularly preferred embodiments, cultures comprised of *L. acidophilus* and *Bifidobacterium* find use.

As used herein, the term "*Lactobacillus*" refers to members of the genus *Lactobacillus*, in the family Lactobacillaceae. These bacteria are Gram-positive facultatively anaerobic bacteria that represent a major part of the bacterial group often referred to as "lactic acid bacteria." Various species of *Lactobacillus* have been identified, including but not limited to *L. acidophilus, L. bulgaricus, L. casei, L. delbrueckii, L. fermentum, L. plantarum, L. reuteri*, etc. While it is not intended that the present invention be limited to any particular species of *Lactobacillus*, in some particularly preferred embodiments, *L. acidophilus* NFCM finds use in the present invention. It is intended that the genus include species that have been reclassified (e.g., due to changes in the speciation of organisms as the result of genetic and other investigations).

As used herein, the term "*Bifidobacterium*" refers to members of the genus *Bifidobacterium*. These bacteria are Gram-positive anaerobic bacteria that are one of the major strains of bacteria present in the gastrointestinal flora. While it is not intended that the present invention be limited to any particular species of *Bifidobacterium*, in some particularly preferred embodiments, *B. lactis* Bl-04 finds use in the present invention. It is intended that the genus include species that have been reclassified (e.g., due to changes in the speciation of organisms as the result of genetic and other investigations).

As used herein, the term "antimicrobial" refers to any compound which inhibits the growth or kills microorganisms. It is intended that the term be used in its broadest sense and includes, but is not limited to compounds such as antibiotics produced naturally or synthetically. It is also intended that the term encompass compounds and elements that are useful for inhibiting the growth of or killing microorganisms.

As used herein, the terms "microbiological media," "culture media," and "media" refer to any suitable substrate for the growth and reproduction of microorganisms. The term encompasses solid plated media, as well as semi-solid and liquid microbial growth systems.

As used herein, the term "fall months" refers to those months commonly recognized as occurring during the fall or autumn. In the northern hemisphere, these months include September, October and November. In the southern hemisphere, these months include March, April and May.

As used herein, the term "winter months" refers to those months commonly recognized as occurring during winter. In the northern hemisphere, these months include December, January and February. In the southern hemisphere, these months include June, July and August.

As used herein, the term "spring months" refers to those months commonly recognized as occurring during the spring. In the northern hemisphere, these months include March, April and May. In the southern hemisphere, these months include September, October and November.

As used herein, the term "summer months" refers to those months commonly recognized as occurring during the summer. In the northern hemisphere, these months include June, July and August. In the southern hemisphere, these months include December, January and February.

Experimental

The following example is provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); $H_2O$ (water); gm (grams); µg and ug (micrograms); mg (milligrams); ng (nanograms); µl and ul (microliters); ml (milliliters); mm (millimeters); nm (nanometers); µm and um (micrometer); M (molar); mM (millimolar); µM and uM (micromolar); U (units); sec (seconds); min(s) (minute/minutes); hr(s) (hour/hours); sd and SD (standard deviation); PBS (phosphate buffered saline [150 mM NaCl, 10 mM sodium phosphate buffer, pH 7.2]); w/v (weight to volume); v/v (volume to volume); CFU (colony forming units); and NCFM (North Carolina Food Microbiology Department); Becton Dickinson (Becton Dickinson Diagnostic Systems, Sparks, Md.); Olympus (Olympus America, Inc., Center Valley, Pa.); Beckman Coulter (Beckman Coulter, Inc., Fullerton, Calif.); Qiagen (Qiagen GmbH, Hilden, Germany); Thermo Biosciences (Thermo Biosciences GmbH, Ulm, Germany; Thermo Electron is the parent company); Applied Biosystems (Applied Biosystems, Cheshire, UK); Difco (Difco Laboratories, Detroit, Mich.); GIBCO BRL or Gibco BRL (Life Technologies, Inc., Gaithersburg, Md.); ATCC (American Type Culture Collection, Manassas, Va.).

The organisms used in the development of the present invention were *L. acidophilus* NCFM and *B. animalis* subsp. *lactis* Bl-04. These strains were grown at commercial large-scale, the strains were grown in fermentation media, harvested by centrifugation and cryostabilized using methods known in the art. The cryostabilized solution was lyophilized. The lyophilized cultures were standardized to provide desired bacterial counts in each culture, using dextrose as a diluent for counting methods performed as known in the art.

A. Study Design

The study design consisted of a randomized, double blind, placebo-controlled study that was conducted over a four month period. Subjects were assigned to the supplemented (i.e., test) (Group 1) and or control (i.e., placebo) (Group 2) groups. The subjects were 48 children, ranging in age from 2 to 10 years, randomly assigned to either probiotic or placebo group. The test group received the probiotic composition, at a daily dose of at least $10^9$ CFU, while the placebo group received rice starch. The study was begun approximately 2 weeks to 1 month before the expected start of the birch pollen allergy season. At the start of the study, the subjects provided samples for determination of base-line faecal and blood sample for further analysis. At predefined intervals during the study, faecal and blood samples were collected.

The success of the test was determined on the basis of frequency of allergic symptoms and the use of medication (antihistamines) against allergy symptoms. It was noted that when respiratory infections occur, medication is often started when there is history of allergies. In addition to reduction in the severity of symptoms and nasal eosinophilia, a decreased frequency of respiratory infections was considered to be a positive outcome of the study.

B. Analysis of Eosinophils

Nasal swabs were collected from each subject at the beginning, mid-point, and end of the present study. The number of eosinophils was determined using selective staining methods known in the art. The results indicated that the nasal eosinophil count was significantly reduced in the treatment group ($p=0.013$). In contrast, there was no difference in the number of bloodstream eosinophils.

C. Analysis of Microbiota

The major groups of faecal bacteria were analyzed using the fluorescent in situ hybridization (FISH) method as known in the art. In brief, fecal samples were suspended in PBS and homogenized. Bacteria were fixed with paraformaldehyde and hybridized with Cy3 indocarbocyanin-labeled oligonucleotide probe. Probes included Bac303 (5'-CCAAT-GTGGGGACCTT; SEQ ID NO:1) for the *Bacteroides-Prevotella* group, Bif164 (5'-CATCCGGCATTACCACCC; SEQ ID NO:2) for bifidobacteria, His150 (5'-TTATGCGG-TATTAAT CT(C/T)CCTTT; SEQ ID NO:3) for clostridia of the *C. histolyticum* group and Lab158 (5'-GGTATTAGCA(T/C)GTGTTTCCA; SEQ ID NO:4) for lactobacilli and enterococci (See e.g., Harmsen et al. J. Pediatr. Gastroenterol. Nutr. 30:61-67 [2000]; and Harmsen et al., FEMS Microbiol. Lett., 183:125-129 [1999]).

Total bacterial counts were determined by staining with 4',6-diamino-2-phenylindole (DAPI). The bacteria were washed and filtered using 0.2 µm polycarbonate filters. The filtered bacteria were then mounted on slides and counted visually under an epifluorescence microscope (Olympus BX51) using Cy3 and DAPI specific filters. At least 15 random fields were counted for each slide and the average count was used for analysis.

In addition, the microbiota were analyzed by in situ hybridization (FISH) combined with flow cytometry (FC-FISH). Hybridization of samples was performed as described above for the FISH analysis. Probes included Bac303 for the *Bacteroides-Prevotella* group, Bif164 for the *Bifidobacterium* group Cy3-labelled and total cells were enumerated using an EUB338 (5'-GCTGCCTCCCGTAGGAGT; SEQ ID NO:5)-fluorescein (FITC)-labelled probe (See, Harmsen et al., [1999] and [2000], supra).

Flow-cytometric analyses were performed using a BDTM LSR II flow cytometer (Becton Dickinson) equipped with four lasers (355, 405, 488 and 635 nm). The 488 nm laser at 15 mW was used. This standard instrument is equipped with two light scatter detectors which measure forward (FSC) and side scatter (SSC) and four fluorescence detectors detecting appropriately filtered light at green (FL1, 525 nm), yellow (FL2, 575 nm), orange (FL3, 620 nm), and red (FL4, 675 nm) wavelengths. To avoid cell coincidence, the flow rate was kept at the lowest setting (data rate 200-300 events per second). At least 30,000 events were recorded for each sample and all experiments were conducted in duplicate. Data were stored as list-mode files and analyzed off-line using the BDTM FACS-Diva software version 4.1.1 (Becton Dickinson).

Immediately prior to analysis, flow-count fluorospheres (Beckman Coulter) were added to each sample. Absolute bacterial cell counts were determined following the manufacturer instructions, using the ratio of positive bacteria to fluorospheres counted using the following formula: cells per microliter=[(cells counted)/(fluorospheres counted)]×fluorospheres/microliter. To avoid loss of the signal intensity of hybridized cells, they were kept in the dark on ice at 4° C. until the flow cytometry assay was conducted. Results were expressed as the numbers of cells hybridizing with the specific group-Cy3 probe and total bacteria EUB 338-FITC probe.

In addition, the microbiota were analyzed by quantitative real-time PCR (qRT-PCR). DNA extractions from pure cultures of the different microorganisms and fecal samples were extracted using the QIAamp DNA stool Mini kit, following the manufacturer's instructions. qPCRs were conducted as known in the art.

For characterization of the fecal microbiota, PCR primers were designed targeting different *Bifidobacterium* species or groups, including the *Bifidobacterium* genus, *B. adolescentis, B. bifidum, B. breve, B. lactis* and *B. longum* group, according to Gueimonde (See, Gueimonde et al., Appl. Environ. Microbiol., 70:4165-4169 [2004]). *L. acidophilus* NCFM was quantified using primers as described by Rousseau (et al. (Rossueaux et al., Nat. Med., 13:35-37 [2007]). The *Bacteroides fragilis* group was determined using methods known in the art (See, Matsuki et al., Appl. Biochem. Microbiol., 68:5445-5451 [2002]). These oligonucleotides were purchased from the Thermo Electron Corporation (Thermo Biosciences). Briefly, PCR amplification and detection were performed with an ABI PRISM 7300-PCR sequence detection system (Applied Biosystems). Each reaction mixture of 25 µl was composed of SYBR® Green PCR Master Mix (Applied Biosystems), 1 µl of each of the specific primers at a concentration of 0.25 µM, and 1 µl of template DNA. The fluorescent products were detected at the last step of each cycle. A melting curve analysis was made after amplification to distinguish the targeted PCR product from the non-targeted PCR product.

D. Cytokine Quantitation

The various cytokines were quantified using commercial ELISA kits obtained from R&D Systems, as per the manufacturer's instructions.

E. Results

Treatment of children with birch pollen allergy with a combination of *B. lactis* Bi-04 and *L. acidophilus* NCFM reduced markers of this type of allergy. In particular, nasal eosinophilia was reduced in the test group, as compared to the control group. In addition, the test group had lower levels of *Bacteroides* sp. in their intestinal microbiota, as compared to the controls. Furthermore, it is contemplated that other immune markers of allergy, including IL-5, IL-10, TGF-β, IFN-γ and IgE will find use in the methods of the present invention as markers of treatment efficacy. It is also contemplated that other markers of allergy will find use in the present invention.

Other aspects of the invention include:

(i) A composition comprising an effective amount of at least one probiotic for use in reducing inflammation and/or eosinophilia associated with exposure to birch pollen. The composition reduces eosinophilia and/or inflammation upon exposure of an individual to birch pollen.

(ii) Use of a composition comprising an effective amount of at least one probiotic in the manufacture of a medicament to reduce inflammation and/or eosinophilia associated with exposure to birch pollen.

(iii) A composition comprising an effective amount of *Lactobacillus acidophilus* and *Bifidobacterium lactis* for use in reducing birch pollen allergy symptoms. The composition reduces birch pollen allergy symptoms, wherein said birch pollen allergy symptoms comprise inflammation and/or eosinophilia.

(iv) Use of a composition comprising an effective amount of *Lactobacillus acidophilus* and *Bifidobacterium lactis* in the manufacture of a medicament to reduce birch pollen allergy symptoms.

(v) Use of a composition comprising an effective amount of *Lactobacillus acidophilus* and *Bifidobacterium lactis* in the manufacture of a medicament to reduce birch pollen allergy symptoms, wherein said birch pollen allergy symptoms comprise inflammation and/or eosinophilia.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

We claim:

1. A method for reducing inflammation and/or eosinophilia associated with exposure to birch pollen comprising administering at least one composition comprising an effective amount of at least one probiotic to an individual having birch pollen induced symptoms comprising eosinophilia and/or inflammation under conditions such that said eosinophilia and/or inflammation are reduced upon exposure of said individual to said birch pollen.

2. The method of claim 1, wherein said eosinophilia is nasal eosinophilia.

3. The method of claim 1, wherein said probiotic comprises a culture of *Lactobacillus*.

4. The method of claim 3, wherein said *Lactobacillus* is *Lactobacillus acidophilus*.

5. The method of claim 3, wherein said probiotic further comprises a culture of *Bifidobacterium*.

6. The method of claim 5, wherein said *Bifidobacterium* is *Bifidobacterium lactis*.

7. The method of claim 1, wherein said individual has birch pollen allergy.

8. The method of claim 1, wherein said individual is a child.

9. The method of claim 1, wherein said administering is nasal or oral.

10. A method for reducing birch pollen allergy symptoms comprising administering a composition comprising an effective amount of *Lactobacillus acidophilus* and *Bifidobacterium lactis* to an individual having birch pollen induced symptoms comprising eosinophilia and/or inflammation under conditions such that said birch pollen allergy symptoms are reduced, wherein said birch pollen allergy symptoms comprise inflammation and/or eosinophilia.

11. The method of claim 10 wherein said eosinophilia is nasal eosinophilia.

12. The method of claim 10 wherein the individual is a child.

13. The method of claim 10 wherein said administering is oral or nasal.

* * * * *